United States Patent [19]

Graham

[11] Patent Number: 4,552,182
[45] Date of Patent: Nov. 12, 1985

[54] HYDRAULIC PULSE DAMPENER EMPLOYING TWO STIFF DIAPHRAGMS AND NESTING MEMBERS

[75] Inventor: Stephen H. Graham, Alameda, Calif.

[73] Assignee: Varian Associates, Inc., Palo Alto, Calif.

[21] Appl. No.: 640,065

[22] Filed: Aug. 13, 1984

Related U.S. Application Data

[62] Division of Ser. No. 487,371, Apr. 21, 1983, abandoned.

[51] Int. Cl.⁴ ............................................. F16L 55/04
[52] U.S. Cl. ..................................................... 138/30
[58] Field of Search .................. 138/26, 30; 220/85 B; 137/207; 210/198.2, 349; 267/114, 118, 122; 417/540; 73/707

[56] References Cited

U.S. PATENT DOCUMENTS

| 852,150 | 4/1907 | Whitney . | |
|---|---|---|---|
| 1,944,340 | 1/1953 | Zubaty et al. | 138/30 X |
| 3,255,779 | 6/1966 | Russell | 138/26 |
| 3,461,914 | 8/1969 | Sugimura et al. | 138/30 |
| 3,601,128 | 8/1971 | Hakim . | |
| 4,129,025 | 12/1978 | Carey . | |
| 4,186,775 | 2/1980 | Muroi . | |
| 4,312,382 | 1/1982 | Gebauer . | |
| 4,427,029 | 1/1984 | Charney et al. | 138/30 |

FOREIGN PATENT DOCUMENTS

| 226 | of 1891 | United Kingdom . |
|---|---|---|
| 1562709 | 3/1980 | United Kingdom . |
| 2115488 | 9/1983 | United Kingdom . |

Primary Examiner—James E. Bryant, III
Attorney, Agent, or Firm—S. Z. Cole; Keiichi Nishimura; David Schnapf

[57] ABSTRACT

A hydraulic pulse dampener has two diaphragms, each positioned opposite a recess formed in the housing. The regions between the diaphragms and the associated recesses are sealed from the fluid which flows through the dampener so that a rise in pressure in the fluid may cause each diaphragm to flex towards the recess behind until it may completely nest in it. The diaphragms are designed differently so that they will begin to flex and take a completely nested position in different pressure ranges.

4 Claims, 12 Drawing Figures

HYDRAULIC PULSE DAMPENER EMPLOYING TWO STIFF DIAPHRAGMS AND NESTING MEMBERS

This application is a division of application Ser. No. 487,371, filed 4/21/83, now abandoned.

This invention relates to a hydraulic pulse dampener for use in liquid chromatographs and, more particularly, relates to a hydraulic pulse dampener for use in a liquid chromatograph which employs a stiff diaphragm which can flex into a nesting member and which absorbs pulse energy and stores it as elastic strain energy.

Pulse dampeners have traditionally been employed in hydraulic systems to dampen pulses. In these systems, pulses have been dampened in order to avoid generating sympathetic harmonic reactions which could damage components or otherwise interfere with the operation of the system. See, e.g., A. Zahid, "Pressure Dampener Device", U.S. Pat. No. 3,782,418, at column 1. In the field of liquid chromatography as the pressures have increased and flow rates have decreased—the domain of high pressure liquid chromatography (HPLC)—there has been a trend towards using reciprocating pumps thereby necessitating the use of such pulse dampeners. Operating pressures have ranged from a few psi to 6000 psi or higher. For HPLC, these pulsations have been sources of damage to columns; they have also interfered with peak elution times since pressure pulsations have associated variations in flow.

In HPLC systems the most common type of pulse dampener employed has been the type that utilizes liquids to absorb the pulse energy as the liquids are compressed. See, for example, P. Y. Achener, "Pulse Damper For High-Pressure Liquid Chromatography", U.S. Pat. No. 4,222,414, and D. R. Boehme, "Pulse Damper", U.S. Pat. No. 4,234,427 (shown in FIG. 1b). Solids have also been used to absorb pulse energy as shown, for example, in J. W. Gatiss, "Pulse Dampers for Liquid Chromatography", U.S. Pat. No. 4,024,061 (shown generally in FIG. 1a). Gas separated from a flowing liquid stream by a diaphragm has also been used to absorb pressure pulses; see A. A. Jacobellia, "High Frequency Pulse Dampener", U.S. Pat. No. 4,163,461, as well as gas-filled bladders; see A. Zahid, "Pressure Pulse Dampener Device", U.S. Pat. No. 3,782,418. And, mechanical means have been used to absorb pulse energy. In K. J. Gildner, "Pulse Dampener", U.S. Pat. No. 3,782,709, and adjustable spring is pressed against a fluid tight diaphragm. The ease with which the diaphragm moves is a function of the tension on this spring at any time. The energy is stored in the spring as the rigid diaphragm transfers pulse energy from the fluid to the spring. The spring constant determines the pressure range in which the dampener is most effective. Another mechanical pulse dampener has been a flexible, resilient, non-circular tube through which a fluid stream flows. As pressure pulses occur, the tube flexes towards a circular shape, thereby increasing volume and alleviating the pressure of the pulse. This is shown in FIG. 1c with cross-section "a" being the normal shape and cross-section "b" being the fully flexed shape. This approach is disclosed in J. L. Waters, "Chromatographic Separation System", U.S. Pat. No. 3,537,585, and in J. G. Nikelly, et al., "Pulse Dampener for High Pressure Liquid Chromatography", Analytical Chemistry, v. 51, p. 1585 (1979).

In the operation of high pressure liquid chromatographs, it has been found necessary to operate over a wide range of pressures in order to accommodate the wide range of flow rates and column resistances. The pressure range is typically from near zero psi to as high as about 6,000 psi. Conventional pulse dampeners of the type which utilize liquids, gases or springs to absorb pulse energy, are not normally suitable for operation over such a large pressure range. While a liquid pulse dampener could be built which would operate over a wide pressure range, the liquid volume would be so large that a very high dead volume would exist, especially at high pressures. This would be detrimental to performance in HPLC.

It is therefore an object of the present invention to provide a pulse dampener for HPLC which provides satisfactory dampening at low pressures.

It is another additional object of the present invention to provide a pulse dampener for HPLC which employs a stiff, flexible diaphragm means that stores energy in elastic strain as the diaphragm nests in a recess.

It is a further object of the present invention to provide a pulse dampener which may be combined with conventional pulse dampening techniques to provide satisfactory dampening over a pressure range from near zero psi to 6,000 psi.

It is an additional object of the present invention to provide a pulse dampener which operates with an optimal dampening constant at low pressures and then adjusts to provide an optimal dampening constant at high pressure.

It is yet another object of the present invention to provide a pulse dampener which no longer expands in volume once the pressure limit of operation is reached.

BRIEF DESCRIPTION OF THE DRAWINGS

For a more complete understanding of the present invention, reference may be had to the accompanying drawings which are incorporated herein by reference and in which:

FIG. 1a illustrates a pulse dampener which functions by compressing a solid;

FIG. 1b illustrates a pulse dampener which functions by compressing a liquid;

FIG. 1c illustrates a pulse dampener which functions by expanding the volume within a tube having a non-circular cross-section;

SUMMARY OF THE INVENTION

Figure 1A:
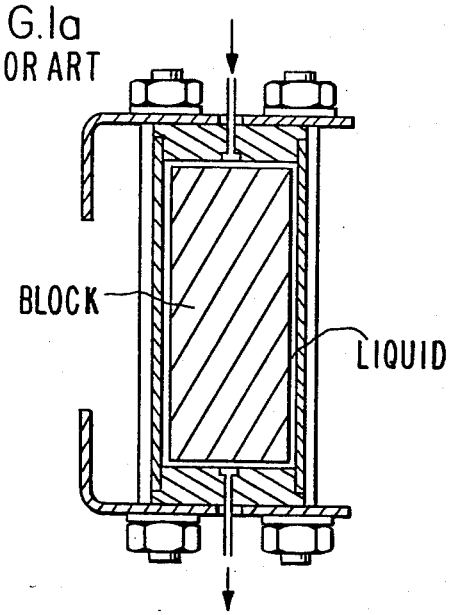
FIGS. 1a–1c illustrate various pulse dampener means of the prior art which are specifically described as follows.
Figure 1B:
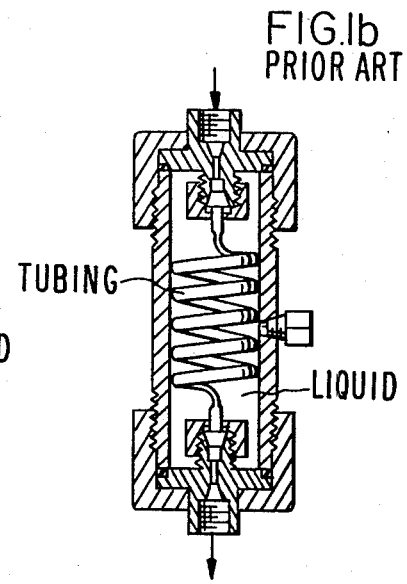
Figure 1C:
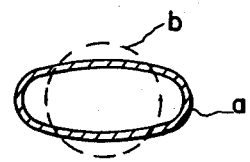

A stiff diaphragm is placed in contact with the pressurized liquid upstream of a high pressure liquid chromatograph. The diaphragm is positioned adjacent a receiving member and when flexed due to absolute increases in pressure or to pressure pulses in the liquid, the diaphragm is capable of nesting in the receiving member. As pressure increases, the diaphragm gradually deforms and nests in the shaped recess. The energy absorbed by the diaphragm increases as the extent of deformation increases. The material, contour and thickness of the diaphragm are all selected so that the deformation occurs for pressures in the regime from near zero to about 1000 psi. In a preferred embodiment, the shape of the nesting member is selected to have a central flat portion which contacts the diaphragm first so that nesting spreads from the center outwardly; thereby producing an increasing resistance to pressure rises as absolute pressure increases. The diaphragm dampener may be used in combination with other conventional pulse dampeners which operate in different pressure regimes, or diaphragm dampeners having multiple diaphragms of different characteristics may be used to obtain operation over an extended pressure range.

DESCRIPTION OF THE PREFERRED EMBODIMENTS

In order to avoid damage to columns and other components and to operate with reproducible peak elution times, it is necessary to dampen pulses in high pressure liquid chromatography systems over a pressure range from a few psi to about 6,000 psi. Conventional pulse dampening techniques which function by compressing liquids, solids or gases, or which store pulse energy mechanically, adequately dampen pulses in pressure above about 1000 psi. The compressibility of these media are typically too high to effectively dampen the pulsations when absolute pressure or pressure pulsations are lower than 1000 psi. Although the volume of the medium to be compressed could be increased to provide for adequate dampening at the lower pressures, this would increase total system volume and would increase the dead volume in the flowing stream at higher pressures; both high system volume and high dead volume are undesirable for HPLC.

The present invention is predicated upon the use of a stiff diaphragm to store in elastic strain energy the energy from pressure pulsations. Energy from increased absolute pressure will also be stored, but this only serves to take up storage capacity. The diaphragm will serve as a pulse dampener so long as its storage capacity has not been used up, i.e., so long as absolute pressure does not exceed some set limit. Below that limit the energy of pressure pulses will be absorbed by the stiff diaphragm as it deforms. The pressure limit is reached when the diaphragm is fully deformed, i.e., when it is fully nested in the receiving member as described subsequently.

The term stiff diaphragm as used in this application means a diaphragm which is not so flexible that no appreciable energy is absorbed as the diaphragm is flexed and not so rigid as to be immovable by the forces exerted by the pressure pulses in the liquid. The stiffness of any diaphragm is determined by the diaphragm material, shape and thickness. As discussed below, these are selected so that the diaphragm gradually deforms as pressure is increased. By properly selecting these quantities, the dampener can be designed to permit effective dampening at low pressures, i.e., at pressures lower than 1000 psi. A receiving member is used with the diaphragm so that the diaphragm nests in a shaped cavity as it flexes. The receiving member is used so that the diaphragm does not rupture at higher pressures and so that unnecessary dead volume is not introduced. In order to accommodate higher pressures as well, a conventional dampener, e.g., one based on the compressibility of a liquid, may be employed in series; alternately, another, stiffer diaphragm may be employed in parallel. In the latter case, the characteristics of the diaphragms are selected so that the first diaphragm will be fully nested in the cavity of the associated receiving member at about the time the second diaphragm begins to flex towards a nesting position.

The pressures that may be damped by the pulse dampener of the present invention can be varied from a few psi to pressures as high as 6000 psi. The range of effective operation will depend upon the thickness and size and upon the tensile strength of the material of the diaphragm. Once a particular diaphragm is fabricated the range of pressures will be fixed. However, as described below, since conventional pulse dampeners function adequately at pressures above about 1000 psi, the special utility of the diaphragm dampener of the present invention exists for pressures below 1000 psi.

Figure 2:
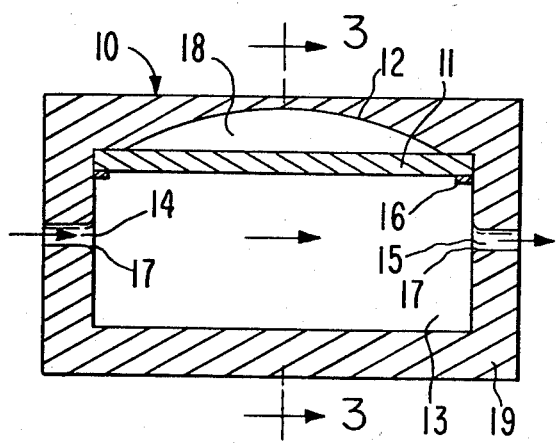
FIG. 2 is a side view of a pulse dampener fabricated in accordance with the present invention.
Figure 3:
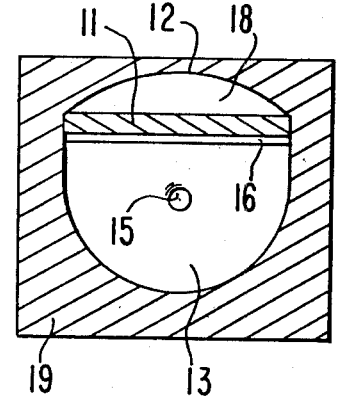
FIG. 3 is a cross-sectional view of the pulse dampener of FIG. 2.

A pulse dampener 10 fabricated in accordance with the present invention is shown in FIGS. 2 and 3. A housing 19 defines a central region 13 for the passage of fluid and the dampening of pressure pulses in the fluid. Fluid is introduced through inlet port 14 and is discharged from outlet port 15. Streamlining contours 17 may be provided at the inlet and outlet in a preferred embodiment to minimize turbulence. A stiff diaphragm 11 is positioned inside housing 19 and held in place, e.g., by lip 16. The diaphragm may be selected from materials such as 17-4 PH Steel, a high carbon steel, tungsten or titanium. The thickness may vary from a few thousandths to a few hundredths of an inch. The diaphragm is fitted sufficiently tightly against the inner wall of housing 19 to isolate recess 18 from the fluid in central region 13. Recess 18 will typically be evacuated or contain only a residual quantity of gas. In operation, as fluid flows in through inlet 14, fills central region 13 and flows out of the dampener through outlet 15, the flowing fluid comes in contact with one surface of diaphragm 11. As pressure from a few tens of psi to a few hundreds of psi is experienced by the diaphragm, there will be a progressive outward flexing. Pulse energy will be stored in elastic strain energy as deviations from average pressure are experienced so long as average or absolute pressure does not exceed the limit where diaphragm 11 is fully nested in recess 18, as discussed previously. At some maximum pressure, either from a pulse or from sustained average pressure, the diaphragm is fully nested in contour 12. If absolute pressure continues to increase or if pulses of a greater amplitude continue, then no further dampening is produced by diaphragm dampener 10.

Figure 4A:
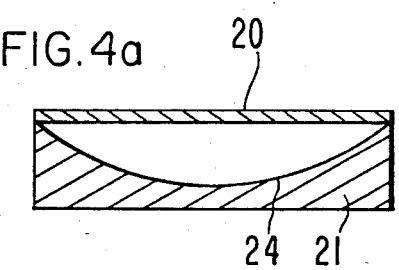
FIGS. 4a–4d are side pictorial views of the stiff diaphragm of the present invention which show the diaphragm as it deforms and nests in a receiving member.
Figure 4B:
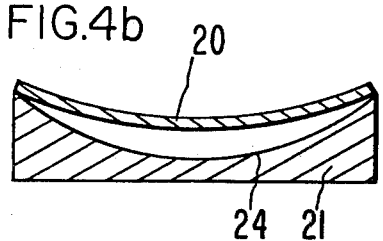
Figure 4C:
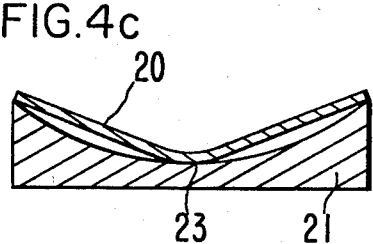

The sequence of flexing for a receiving member of a particular configuration is shown in FIGS. 4a–4d. In FIG. 4a, stiff diaphragm 20 has not experienced sufficient pressure to produce any deformation. It is supported at its edges by receiving member 21 and rests above shaped recess 24. In FIG. 4b, diaphragm 20 has experienced sufficient pressure to flex towards recess 24 in receiving member 21. In FIG. 4c, the middle of diaphragm 20 has contacted recess 24 at point 23. As average pressure continues to increase, or as pressure pulses are experienced, diaphragm 20 is deformed further in the regions between the midpoint 23 and the edges of receiving member 21 until diaphragm 20 fully nests in recess 24. Additional increases in pressure produce no additional deformation. At this point no additional dampening is provided by the diaphragm dampener. The resistance to deformation increases progressively after midpoint 23 is contacted. The gradual increase in resistance to deformation as pressure increases allows the diaphragm to continue damping at higher and higher pressure regimes. The increase in resistance (or stiffness) of the diaphragm is caused by shaping the recess to provide more and more support as the pressure forces the diaphragm further into the recess; the area of the diaphragm susceptible to flexing becomes progressivley less and less. In other embodiments, various shapes, thicknesses and materials may be selected for the diaphragm and specific contours may be selected for the recess to tailor the resistance of the diaphragm to increasing pressure. A wide range of profiles of resistance as a function of pressure may be produced. The mechanical characteristics of such generalized diaphragms are known. See, for example, the tables in Chapter 10 of Roark and Young, *Formulas for Stress and Strain*, (1975).

As the diaphragm deforms, volume increases and the capacity of the system is increased, thereby decreasing pressure. This is reflected in the formula applicable to all pulse dampeners which use liquid as the energy storage media:

For a liquid compressibility dampener
where:

$$P/P_0 = \exp(-\tau/Rc)$$

where
C=XV
Po=pressure at peak of pulse
P=pressure at bottom of pulse
C=capacity of the dampener
V=system volume+fluid volume in pulse damper
R=hydraulic resistance, pressure/flow rate
$\tau$=duration damper must supply flow system pressure
X=spring constant of fluid For a dipahragm dampener $$\frac{P}{P_0} = \exp\left(\frac{[-32t^3\tau]}{2\pi R a^\theta (1 - \gamma^2)}\right)$$

Figure 4D:
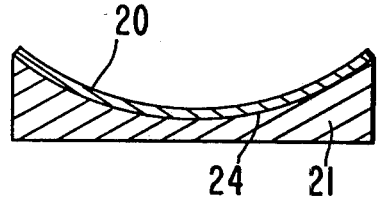
Figure 5:
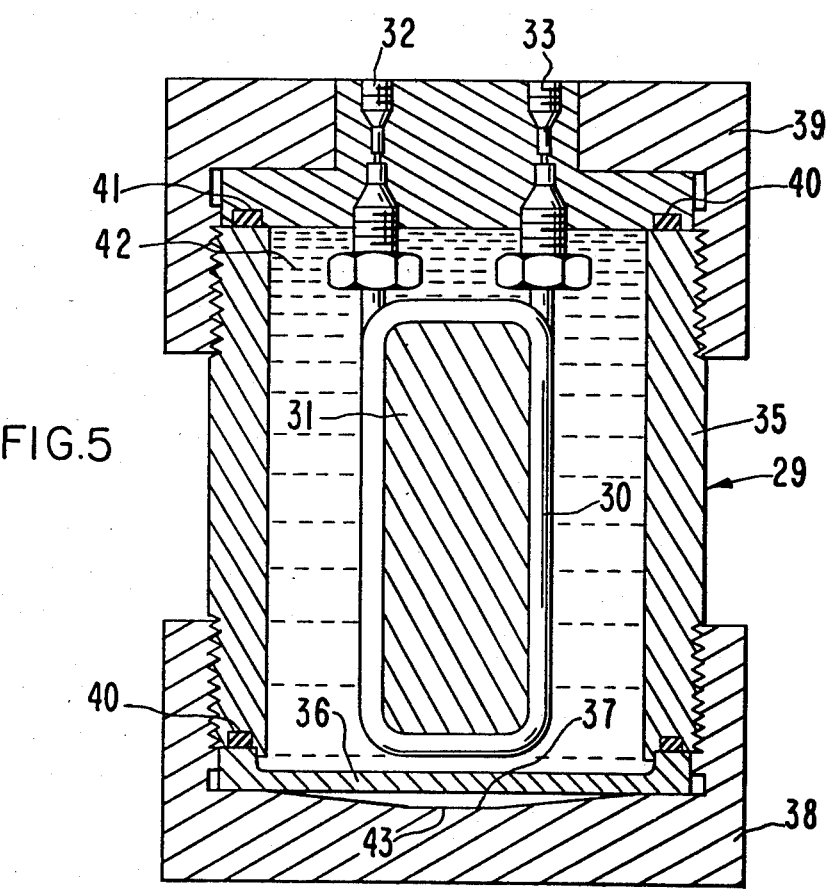
FIG. 5 is a cross-sectional view of an alternate embodiment of the present invention which also utilizes a conventional pulse dampener employing liquid compressibility.

Capacitance $$C = \frac{-32t^3}{2\pi a^\theta (1 - \gamma^2)}$$

t=diaphragm thickness
$\tau$=duration damper must supply flow system pressure
a=diaphragm diameter
R=column resistance
$\gamma$=poisson ratio
P=pressure at end of pulse duration
Po=pressure at beginning of pulse duration As shown in FIGS. 4c and 4d, prior to becoming fully nested, the diaphragm 36 provides increasing resistance to incremental rises in pressure due to the gradual nesting of diaphragm 20 in recess 24. Gradual nesting is aided, for example, by the flat bottom 43 of recess 38 as shown in FIG. 5.

Figure 6:
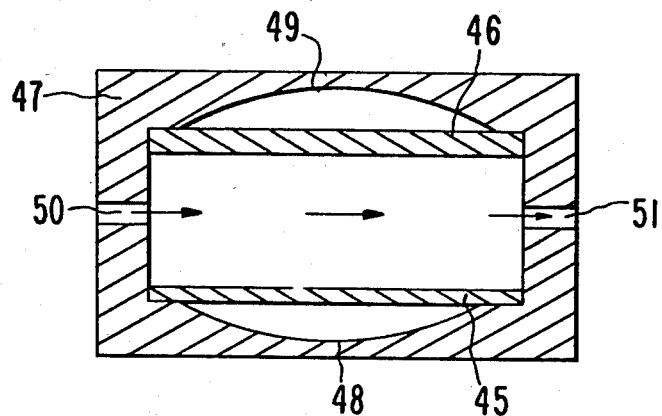
FIG. 6 is a side view of yet another embodiment of the present invention, which employs two diaphragms, each having a different thickness and stiffness to provide damping over a wide pressure range.

A further embodiment of the present invention is shown in FIG. 6. Within housing 47 two diaphragms 45 and 46 are separately positioned. Fluid flows through inlet port 50 and exits outlet port 51. Each of the diaphragms 45,46 is fixed in position opposite an associated recess 48,49. Each diaphragm functions as an individual unit as described previously. However, the size and shape of each diaphragm is selected so that it performs optimally in a particular pressure range. Typically, the ranges are selected to be complementary. Thus, for diaphragms 45,46 of the same shape and fabricated from the same material, the thinner dampener 45 will operate in a lower pressure range, e.g., from near zero to about 700 psi, and the thicker dampener will operate in a higher pressure range, e.g., from about 500 to about 1200 psi.

Figure 7:
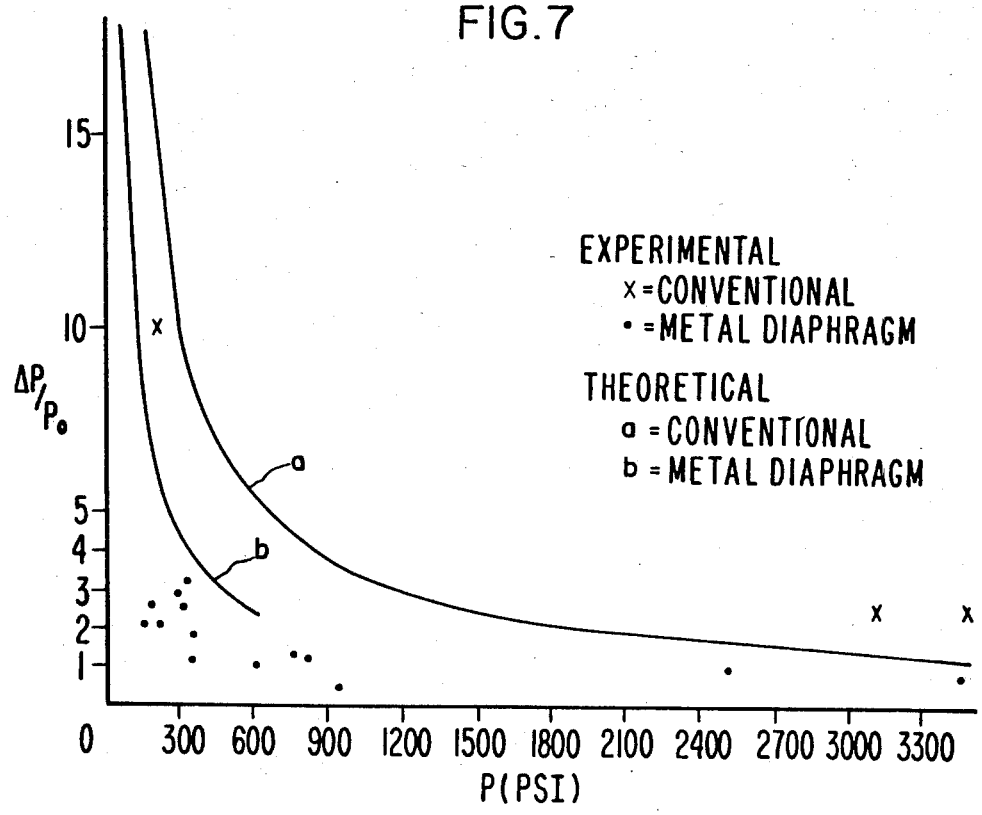
FIG. 7 is a graph showing the predicted and actual performance for a conventional pulse dampener and for the pulse dampener of the present invention.

The configuration of FIG. 6 permits a broad pressure range to be serviced by the dampener. This is especially advantageous since conventional dampeners operate effectively at pressures higher than about 1000 psi and the diaphragm operates well at lower pressures. As seen from curve b in FIG. 7, the diaphragm dampener can be designed to operate effectively at pressures well below 800 psi. Thus, pressure pulsations can be maintained very low at low pressures. Conventional dampeners, on the other hand, as seen from curve a operate most effectively for higher pressures out to several thousand psi.

What is claimed is:

1. A hydraulic pulse dampener, comprising:
   a fluid-tight housing having an inlet port for introduction of a fluid into said housing, an outlet port for discharge of said fluid from said housing, and a first recess and a second recess, and
   a first diaphragm and a second diaphragm positioned separately within said housing adjacent respectively said first and second recesses, the region between said first diaphragm and said first recess and the region between said second diaphragm and said second recess being sealed from said fluid, both diaphragms being made of a material that will flex towards said recesses to assume a nesting position therein at some predetermined rise in pressure of said fluid, absorb hydraulic pulse energy of said fluid and store the energy as elastic strain energy, wherein the diaphragms have different flexibility so that they assume nesting positions at different pressure levels.

2. The dampener of claim 1 wherein said fluid is adapted to flow inside said housing directly in contact with said first and second diaphragms.

3. The dampener of claim 1 wherein said sealed regions are evacuated.

4. The dampener of claim 1 wherein each of said recesses is contoured such that the proportion of the diaphragm which is nested within said recess varies in a predetermined manner within a predetermined range of pressure, whereby at the lowest pressure of said range of pressure only a small portion of said diaphragm is nested within said recess, while at the highest pressure of said range of pressure the diaphragm is fully nested within said recess.

* * * * *